United States Patent [19]

Calame-Lonjean et al.

[11] Patent Number: 4,512,203
[45] Date of Patent: Apr. 23, 1985

[54] LIQUID SAMPLING DEVICE

[75] Inventors: André Calame-Lonjean, Bagnols sur Ceze; Pierre Naujalis, Orly, both of France

[73] Assignee: Commissariat a l'Energie Atomique, Paris, France

[21] Appl. No.: 435,274

[22] Filed: Oct. 19, 1982

[30] Foreign Application Priority Data

Oct. 26, 1981 [FR] France .................. 81 20038

[51] Int. Cl.³ .............................. G01N 1/14
[52] U.S. Cl. .................. 73/863.81; 73/864.31; 73/864.34; 73/864.52; 141/130
[58] Field of Search ........... 73/864.52, 863.81, 864.34, 73/864.31, 864; 141/130, 113

[56] References Cited

U.S. PATENT DOCUMENTS 4,160,382 7/1979 Finsterwalder .................. 141/130

FOREIGN PATENT DOCUMENTS 1437674 3/1966 France .
1543691 9/1968 France .
2347671 11/1977 France .

Primary Examiner—S. Clement Swisher
Attorney, Agent, or Firm—Oblon, Fisher, Spivak, McClelland & Maier

[57] ABSTRACT

The present invention relates to a liquid sampling device of the type having at least one hollow needle mounted on an end fitting, which is itself disposed on a support having a supply pipe and a discharge pipe of the liquid to be sampled and between which there is an intermediate tank. The device has a drainage duct connecting the lower part of the intermediate tank to the supply pipe, whilst the lower part of the end fitting is in the form of a sleeve, immersed in the intermediate tank and open at its lower end. The invention is useful for the sampling of radioactive liquids in the nuclear industry.

12 Claims, 7 Drawing Figures

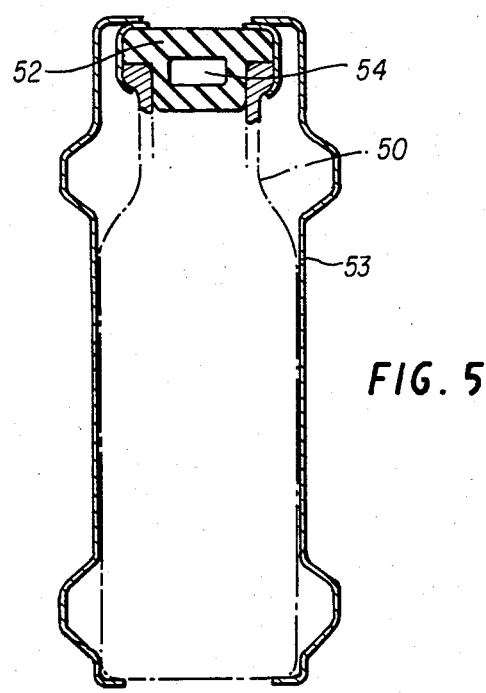
FIG. 5
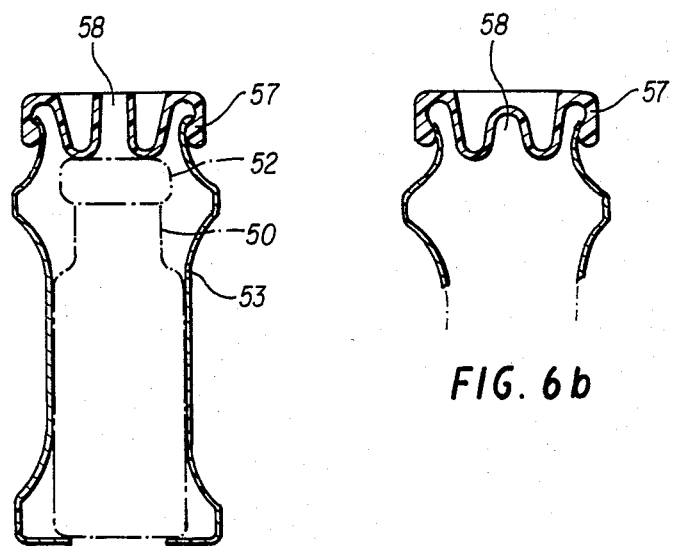
FIG. 6b
FIG. 6a

LIQUID SAMPLING DEVICE

BACKGROUND OF THE INVENTION

The present invention relates to a device for taking liquid samples, permitting in particular a good homogenization of the liquid to be analysed, as well as to a sampling bench using such a device.

In nuclear installations, when it is desired to take radioactive liquid samples for analysis purposes, the standard method consists of using a hollow needle, connected to a storage tank of the liquid to be analysed and on which is pierced a container or jug, provided with an elastic plug. As this container has been previously placed under vacuum, it automatically fills with the liquid by suction. The vessels containing the liquids to be sampled are located under protective means, at distances. of often several dozen meters, so that it is necessary to raise the liquid up to the location where sampling is to take place. Various types of devices have been used hitherto, as a function of the distance between the sampling point and the vessel containing the liquid to be analysed.

In the case of short distances (2 to 5 m) a needle, e.g. having an internal diameter of 1.2 mm and a thickness of 0.5 mm, directly connects the sampling point to the vessel containing the liquid to be sampled. No homogenization of the liquid is possible in such a device, which is obviously prejudicial to the presentativeness of the analysis. In addition, deposits can occur within the needle and the raised liquid can dissolve the deposits which occur during the previous sampling operation, which further falsifies the measurements.

For greater distances and level differences, the liquid is raised into intermediate tanks by vacuum action. The closest tank to the sampling point has a small volume cavity in which is located the end of the needle. It is possible to perform a rinsing of the installation up to the level of the cavity by a sequence of raising and draining operations, but level with the needle, it is not always possible to carry out an adequate homogenization and prevent unwanted deposits.

Systems involving the continuous circulation of liquids by airlift have also been used. In this way, there is a continuous circulation of the liquid from the storage tank to the cavity, in which the end of the needle is located. This ensures a good homogenization of the liquid as a result of the circulation and the latter permits an effective rinsing of the pipes. However, at the actual needle, there are still risks of deposits taking place. In addition, airlift systems have been used in which a circulation of the liquid takes place in the actual container, as a result of a sampling device having two needles connected to the liquid supply and discharge tubes. Although this ensures homogenization and rinsing of the circuit, this system only has a limited efficiency level.

Another system also uses a liquid circulation by airlift, but the airlift head has a small tank positioned between the small diameter supply tube and the larger diameter return tube. The liquid arriving by the small tube is discharged into the tank which, once full, overflows into the return tube. An orifice connects the lower part of the intermediate tank to the discharge tube, in order to ensure emptying when the installation is stopped. However, despite the presence of this orifice, unwanted deposits are still possible in the intermediate tank.

BRIEF SUMMARY OF THE INVENTION

The object of the present invention is a sampling device, which obviates these disadvantages and permits an excellent homogenization of the liquid to be sampled and ensures a very effective draining during the stoppage of the installation.

According to a main feature of the device for taking liquid samples according to the invention, which is of the type having at least one hollow needle mounted on an end fitting, which is itself disposed on a support having an intake pipe and a discharge pipe for the liquid to be sampled, between which there is an intermediate tank, said device has a drainage duct connecting the lower part of the intermediate tank to the supply pipe, whilst the lower part of the end fitting is in the form of a sleeve immersed in said intermediate tank and open at its lower end.

The presence of a duct between the intermediate tank and the supply tube permits, besides a very effective draining during a stoppage of the installation, a permanent renewal and homogenization of the liquid in the intermediate tank. The sleeve immersed in the latter serves to prevent turbulence caused by the reentry of air into the needle, when using a vacuum airlift circulation system.

The invention also relates to a sampling bench using a device having needle end fittings, like that described hereinbefore.

According to the main feature of this sampling bench, it has a fixed base on which a certain number of needle end fittings are distributed in accordance with at least one circumferential arc, a supply station and a discharge station for the containers positioned on said circumferential arc, the base also having a fixed toothed ring and a pivot, whose axes coincide with that of the said circumference, the pivot supporting a rotary arm.

According to a preferred embodiment of such a sampling bench, the containers are disposed within receptacles, called slides, permitting their transfer within the bench by pneumatic systems. In certain cases, the slides can be equipped with a polythene cap, which can be sealed by welding, whose function will be described hereinafter.

Optionally, it is possible to place on the fixed base, a weighing station for the containers after sampling and a welding station for closing the cap, sealing the slides, said two stations being located on the circumference defined by the hollow needle end fittings.

According to another feature of this bench, the rotary arm has a pinion actuated by a geared motor and which meshes on the fixed toothed ring. A locking device using a moving finger is able to penetrate cavities provided on the fixed toothed ring and a tool holder having at least one sampling tool and a needle disassembly tool are also provided.

BRIEF DESCRIPTION OF THE DRAWINGS

The invention is described in greater detail hereinafter relative to non-limitative embodiments and the attached drawings, wherein:

FIG. 5 shows a diagrammatic sectional view of a container placed within a slide.

FIGS. 6a and 6b show views similar to FIG. 5 showing how a slide can be closed by a polythene cap, which can be sealed by welding.

DETAILED DESCRIPTION OF THE PREFERRED EMBODIMENTS

Figure 1:
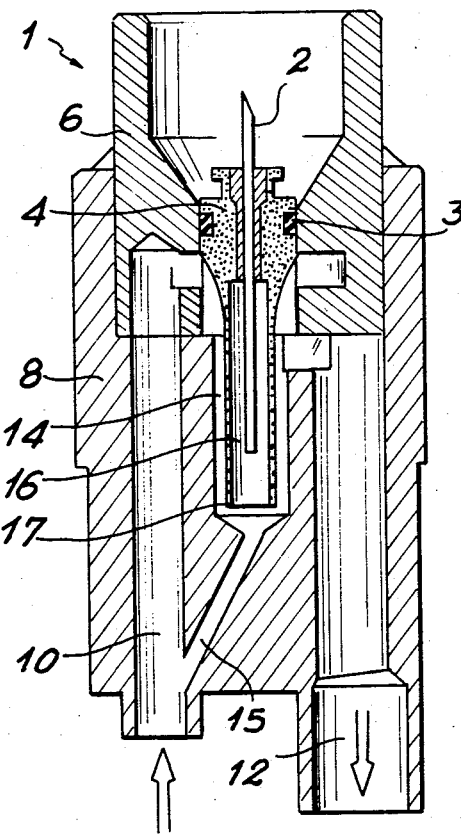
FIG. 1 shows a diagrammatic vertical sectional view of a sampling device according to the invention having only a single hollow needle.

FIG. 1 shows in diagrammatic sectional form, a liquid sampling device according to the invention. This device, carrying the general reference 1, comprises a hollow needle 2 mounted on an end fitting 4, which is itself disposed within a plug 6. An O-ring 3 ensures the sealing between end fitting 4 and plug 6. The latter is mounted within a support 8, provided with a supply pipe 10 and a discharge pipe 12 for the liquid to be sampled. An intermediate tank 14 is positioned at the centre of support 8 between supply pipe 10 and discharge pipe 12. It is also possible to see a drainage duct 15 in the form of a small diameter, highly inclined duct, connecting the bottom of the intermediate tank 14 and supply pipe 10. The lower part of end fitting 4 is extended by a cylindrical sleeve 16, whose length is roughly equal to that of the intermediate tank 40, said sleeve being open at its lower end 17.

On circulating the liquid to be analysed, e.g. by means of an airlift system, the same enters the intermediate tank 14, both via the upper part thereof through the supply pipe 10 and through the lower part thereof by means of duct 15. This arrangement permits a constant renewal and homogenization of the liquid throughout the sampling operation. Sleeve 16 has a calming function, in order to prevent possible turbulence caused within tank 14 by the reentry of air, due to the vacuum effect of the air lift. The turbulence could lead to inadmissible vibrations of the sampling needle. Apart from the fact that duct 15 ensures a good homogenization of the liquid by enabling it to enter tank 14 at two different points, it ensures a very effective drainage during the stoppage of the installation, as a result of its very pronounced slope.

Figure 2:
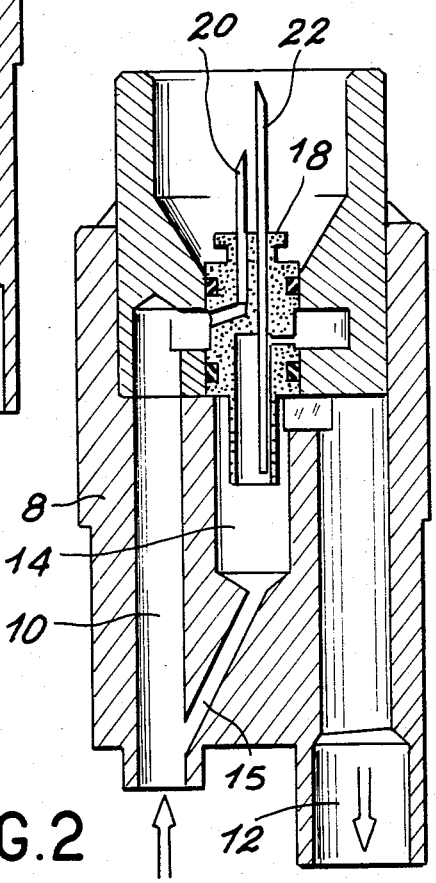
FIG. 2 shows a view similar to that of FIG. 1 of a device having two hollow needles.

FIG. 2 shows a device similar to that of FIG. 1 in which it is possible to see support 8 with intake pipe 10 and discharge pipe 12, together with the intermediate tank 14 and drainage duct 15. However, end fitting 18 carries two hollow needles of different lengths, whereof the shorter needle 20 is connected to supply pipe 10 and the longer needle 22 to discharge pipe 12. This arrangement makes it possible to complete the homogenization of the liquid by making it circulate in the container, when the latter is perforated on needles 20 and 22.

The invention also relates to a sampling bench for taking radioactive liquid samples using hollow needle devices, like that described hereinbefore.

Figure 3:
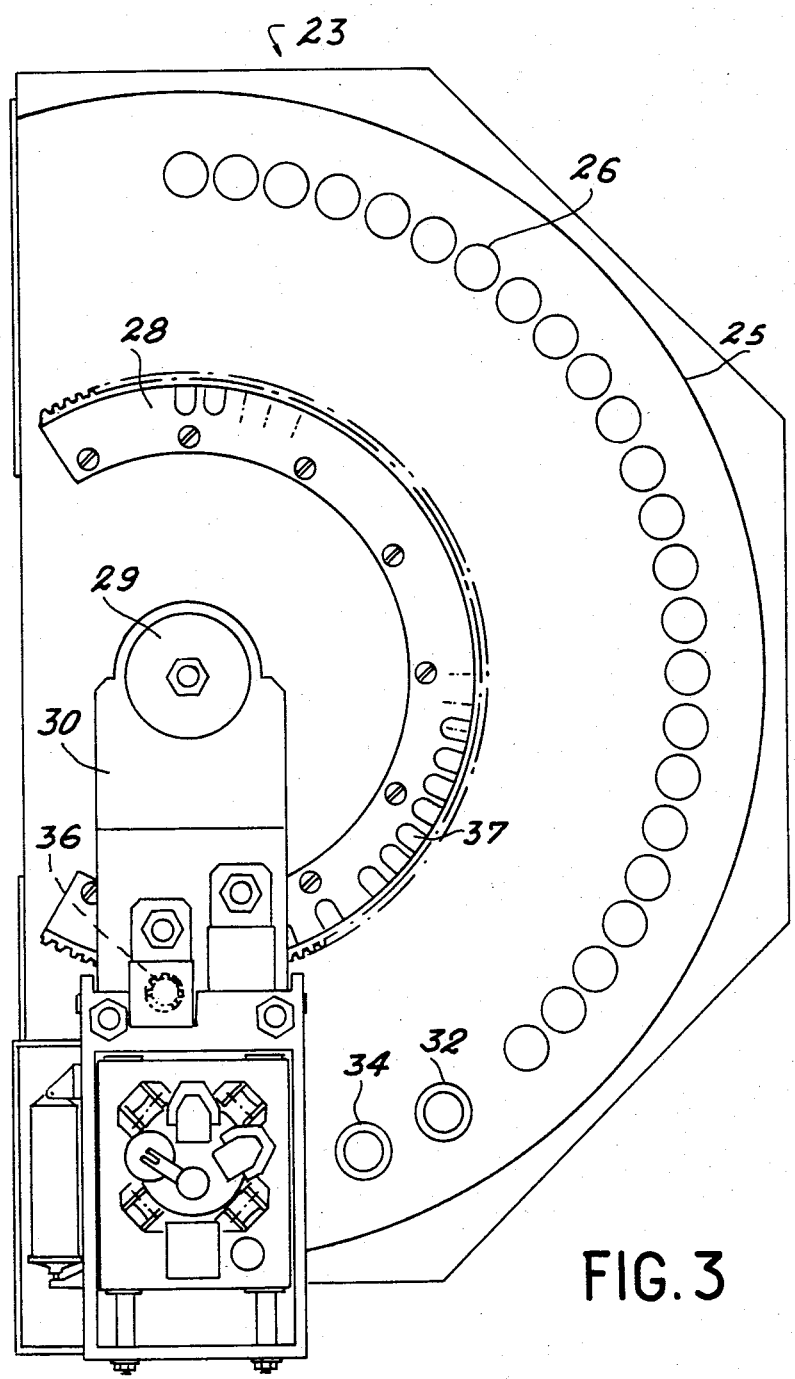
FIG. 3 shows a plan view of a sampling bench using a certain number of hollow needle devices according to the invention, viewed from the direction of arrow F of FIG. 4.

FIG. 3 is a plan view of such an apparatus. It is possible to see that bench 23 firstly comprises a fixed base 25, over which are distributed a plurality of sampling devices 26, like that described hereinbefore. The various devices 26 are arranged in accordance with a circumferential arc. Base 25 also has a fixed circular toothed ring 28 in the centre of which is disposed a pivot 29, which supports a rotary arm 30. The rotation axis of pivot 29 intersects the plane of base 25 in the centre of ring 28, which coincides with the centre of the circle defined by devices 26. On the said circle, there are also provided a station 32 for weighing the containers after sampling and a welding station 34, whose function will be described hereinafter. The rotary arm 30 moves around its axis, as a result of a pinion 36, which can engage on the teeth of ring 28. It can be immobilized by locking in a given position, as a result of a vertically movable index that can penetrate cavities 37 made on ring 28.

Figure 4:
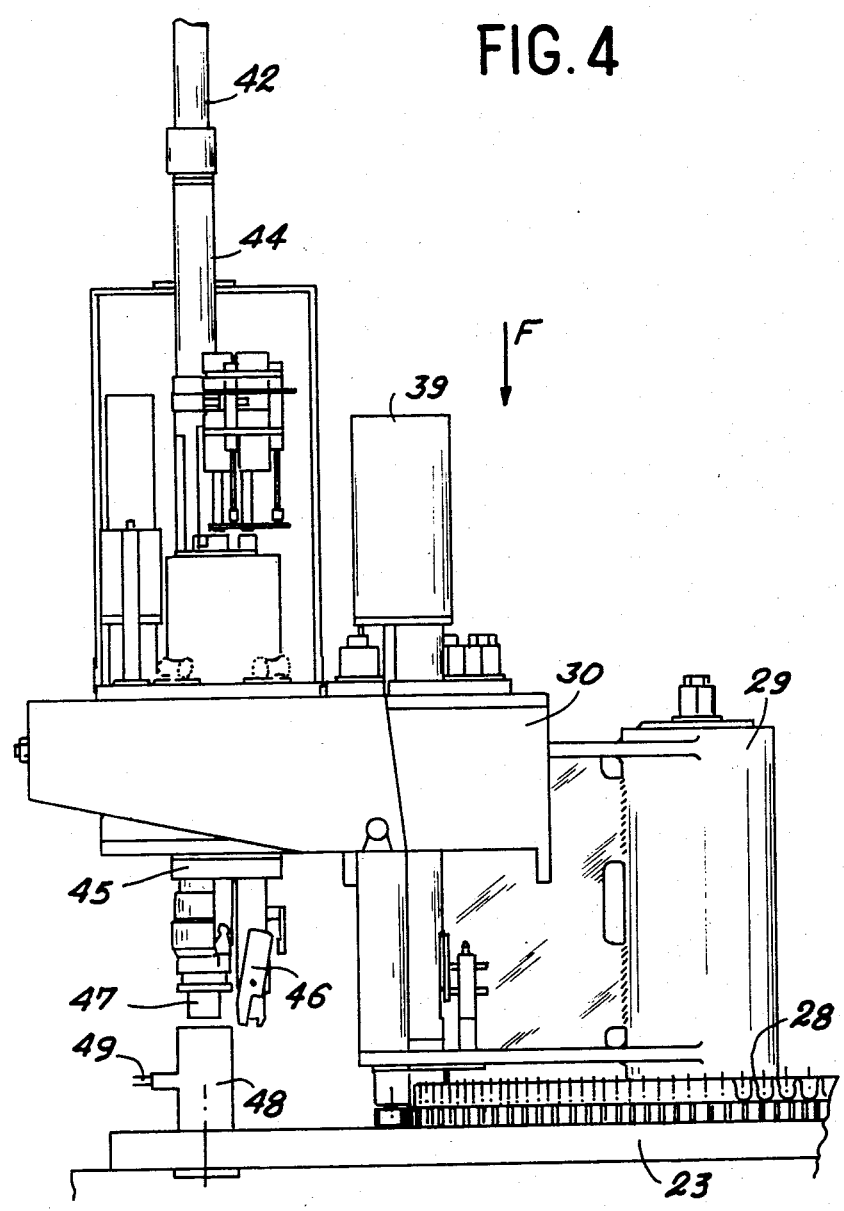
FIG. 4 shows an elevation of the sampling bench.

Pinion 36 is moved by means of a geared motor 39, which can be seen in FIG. 4. FIG. 4 also shows a tube 42, permitting the entry of the containers by pneumatic transfer, the latter being placed within slides. From tube 42, the container-slide assemblies drop into a tube 44 integral with rotary arm 30 and from there reach the supply station (not shown in FIG. 4) positioned on base 25. A drum or cylinder 45, placed in the lower part of moving arm 30, permits, by rotation, the bringing of the sampling tool 46 into a position above the container, which is then brought above any random device 26 by rotating arm 30 about pivot 29. Once sampling has taken place, the container is brought to the discharge station 48, which is in the form of a cylinder, provided with a compressed air intake 49 for the pneumatic transfer.

As stated hereinbefore, each container is placed within a slide, like that shown in FIG. 5. It is possible to see in FIG. 5 a container 50, shown by dot-dash lines, whose upper part is sealed by an elastic plug 52. A sleeve or slide 53 surrounds container 50 and permits its pneumatic transfer in the installation, both before and after sampling, whereas in the prior art sampling benches, the containers could only be introduced into the slides after sampling. In the special case of FIG. 5, the elastic plug 52 of slide 50 has an inner cavity 54, which is not connected to the outside. The function of the cavity is to hold back the liquid drop which remains on the plug after the perforation thereof by the needle and which can be a dangerous source of contamination.

FIGS. 6a and 6b illustrate another method making it possible to hold back this drop. In FIG. 6a, it is possible to see container 50 within slide 53, but the end of the latter corresponding to plug 52 of slide 50 is provided with a polythene cap 57, whose central part is in the form of a passage 58, permitting the passage of the needle for perforating plug 52. When the container is removed from the needle, passage 58 is closed by welding, e.g. ultrasonic welding, in the manner indicated in FIG. 6b. This operation takes place on the welding station 34 of the aforementioned sampling bench (cf FIGS. 3 and 4). This obviates any contamination by the said drop.

The sampling device according to the invention has particularly interesting advantages, because it permits a good homogenization of the liquid to be sampled and an effective rinsing of the installation, which guarantees a good representativeness of the samples of liquid taken.

Finally, although a particular sampling bench in which such devices can be advantageously used has been described, they can be used in any random bench in which the liquid to be sampled is continuously circulated.

What is claimed is:

1. A liquid sampling device comprising
   a support comprising a supply pipe for a liquid to be sampled, a discharge pipe for said liquid, an intermediate tank, and drainage means for said liquid connecting a lower part of said intermediate tank and said supply pipe, an end fitting held by said support, a lower portion of said end fitting comprising a sleeve immersed in said intermediate tank, a lower end of said sleeve being open, and at least one hollow needle held by said end fitting.

2. A liquid sampling device as claimed in claim 1, wherein said liquid sampling device comprises a single hollow needle.

3. A liquid sampling device as claimed in claim 1, further comprising a second hollow needle of different length from said at least one hollow needle, said second hollow needle being held by said end fitting wherein the shorter of said needles is in communication with said supply pipe and the longer of said needles is in communication with said discharge pipe.

4. A liquid sampling device as claimed in claim 1, wherein said supply pipe further comprises a first opening at which said drainage means connects with said supply pipe and a second opening remote from said first opening, said supply pipe being in communication with a lower end of said at least one needle through said second opening.

5. A liquid sampling bench for filling containers with a sampled liquid, said bench comprising at least one liquid sampling device, said liquid sampling device comprising a support comprising a supply pipe for a liquid to be sampled, a discharge pipe for said liquid, an intermediate tank, and drainage means for said liquid connecting a lower part of said intermediate tank and said supply pipe, an end fitting held by said support, a lower portion of said end fitting comprising a sleeve immersed in said intermediate tank, a lower end of said sleeve being open, and at least one hollow needle held by said end fitting, said liquid sampling bench further comprising movable arm means for positioning said containers above said liquid sampling device in operative engagement therewith.

6. A liquid sampling bench as claimed in claim 5, further comprising a fixed base, said movable arm means being pivotally mounted to said fixed base about a pivot axis perpendicular to said fixed base, a plurality of said liquid sampling devices disposed on said fixed base in an arc centered on said pivot axis, wherein said movable arm means further comprises handling means for receiving said containers, for moving one of said containers and selectively positioning said container above one of said plurality of sampling devices in operative engagement therewith, and for thereafter discharging said container, a supply station for feeding said containers to said handling means, and a discharge station for receiving containers from said handling means.

7. A liquid sampling bench as claimed in claim 6, further comprising a container weighing station disposed on said fixed base and on said arc defined by said plurality of said liquid sampling devices.

8. A liquid sampling bench as claimed in one of claims 6 or 7, further comprising a welding station disposed on said fixed base and on said arc defined by said plurality of said liquid sampling devices.

9. A liquid sampling bench as claimed in claim 6, further comprising an arcuate toothed ring fixedly mounted to said fixed base, and centered on said pivot axis, said toothed ring comprising a plurality of cavities, and wherein said movable arm means further comprises a pinion engaged with teeth of said tooted ring, geared motor means for rotatably driving said pinion to cause said movable arm means to pivot about said pivot axis, a locking device for selectively engaging with one of said cavities to prevent said pivoting movement of said movable arm means about said pivot axis, at least one sampling tool for engaging and handling a container, said at least one sampling tool being mounted to a tool holder, and a tool for dismantling said needles of said plurality of said liquid sampling devices.

10. A liquid sampling bench as claimed in claim 6, wherein an opening of said container is closed by an elastic plug, said container being disposed within individual slide means for aiding in transporting said container, said individual slide means comprising an opening proximate said elastic plug.

11. A liquid sampling bench as claimed in claim 10, wherein said elastic plug further comprises means for allowing penetration by one of said needles and further comprises an inner cavity disposed completely within said plug in a position to be traversed by said needle during said penetration.

12. A liquid sampling bench as claimed in claim 10, wherein said individual slide means further comprises a cap disposed in said opening of said slide means proximate said elastic plug, said cap comprising a passage for the passage of one of said needles, said passage being configured so as to be closable by deformation of said cap.

* * * * *